US008627432B2

(12) United States Patent
Dachiraju et al.

(10) Patent No.: US 8,627,432 B2
(45) Date of Patent: Jan. 7, 2014

(54) WEB BROWSER PLAYBACK FOR A VIDEO PROVISIONING SYSTEM

(75) Inventors: Nageswara Raju Dachiraju, Irving, TX (US); Sampath K. Nambakkam, Irving, TX (US); Nagaviswas Ventrapragada, Coppell, TX (US); Velmurugan Krishnaswamy, Irving, TX (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 65 days.

(21) Appl. No.: 13/207,150

(22) Filed: Aug. 10, 2011

(65) Prior Publication Data
US 2012/0079578 A1  Mar. 29, 2012

Related U.S. Application Data

(60) Provisional application No. 61/387,939, filed on Sep. 29, 2010.

(51) Int. Cl.
*H04L 29/06* (2006.01)
(52) U.S. Cl.
USPC ........ 726/7; 726/9; 713/159; 705/51; 705/52; 705/53; 705/57; 705/59
(58) Field of Classification Search
USPC ................................................ 726/7; 705/65
See application file for complete search history.

(56) References Cited

U.S. PATENT DOCUMENTS

| 2008/0215467 | A1* | 9/2008 | Huffman et al. ................ 705/30 |
| 2009/0199287 | A1* | 8/2009 | Vantalon et al. .................. 726/9 |
| 2010/0161973 | A1* | 6/2010 | Chin et al. ..................... 713/159 |
| 2010/0211776 | A1* | 8/2010 | Gunaseelan et al. .......... 713/165 |
| 2010/0250389 | A1* | 9/2010 | Augustin et al. ................. 705/26 |
| 2011/0047566 | A1* | 2/2011 | Matuchniak et al. ............ 725/29 |
| 2011/0075990 | A1* | 3/2011 | Eyer ............................. 386/241 |
| 2011/0268178 | A1* | 11/2011 | Park et al. ................ 375/240.02 |
| 2012/0030554 | A1* | 2/2012 | Toya ............................. 715/206 |

OTHER PUBLICATIONS

Sanchez et al., "An Access Control System for Multimedia Content Distribution", 2006, pp. 169-183.*

* cited by examiner

*Primary Examiner* — David Pearson
*Assistant Examiner* — Thaddeus Plecha

(57) ABSTRACT

A method, performed by a video provisioning system, may include receiving a request for a first digital rights management (DRM) token, associated with a video asset purchased via the video provisioning system, from a browser application associated with a user device and providing the first DRM token to the browser application. The method may further include receiving a license authorization request to issue a DRM license for the video asset, where the license authorization request is received from a license server, where the DRM license is to be used by the user device to decrypt the video asset, and where the license authorization request includes a second DRM token; determining whether the second DRM token matches the first DRM token; and authorizing the license server to issue the DRM license for the video asset, when the second DRM token matches the first DRM token.

15 Claims, 9 Drawing Sheets

WEB BROWSER PLAYBACK FOR A VIDEO PROVISIONING SYSTEM

REFERENCE TO RELATED APPLICATION

This application claims priority to U.S. Provisional Patent Application No. 61/387,939, filed Sep. 29, 2010, the entire contents of the provisional application being incorporated herein by reference.

BACKGROUND INFORMATION

Video content may be available from many sources and may be delivered to users through a variety of methods. For example, video content may be available from commercial broadcasting television networks (e.g., ABC, CBS, NBC, FOX, etc.) via free broadcast; from a cable television service (e.g., CNN, TNT, TBS, etc.) for a periodic subscription fee; from a satellite television service (e.g. DirectTV, Dish Network, etc.) for a periodic subscription fee; from a pay-per-view service; from an on-demand video service; from a over-the-top (OTT) content providers on the Internet (e.g., Hulu, Veoh, Jaman, YouTube, etc.); and/or from any other commercial supplier (e.g., iTunes, Netflix, Blockbuster, etc.). Video content may be delivered to users, for example, via a set top box, a computer device, a wireless mobile device.

DETAILED DESCRIPTION OF PREFERRED EMBODIMENTS

Figure 1:
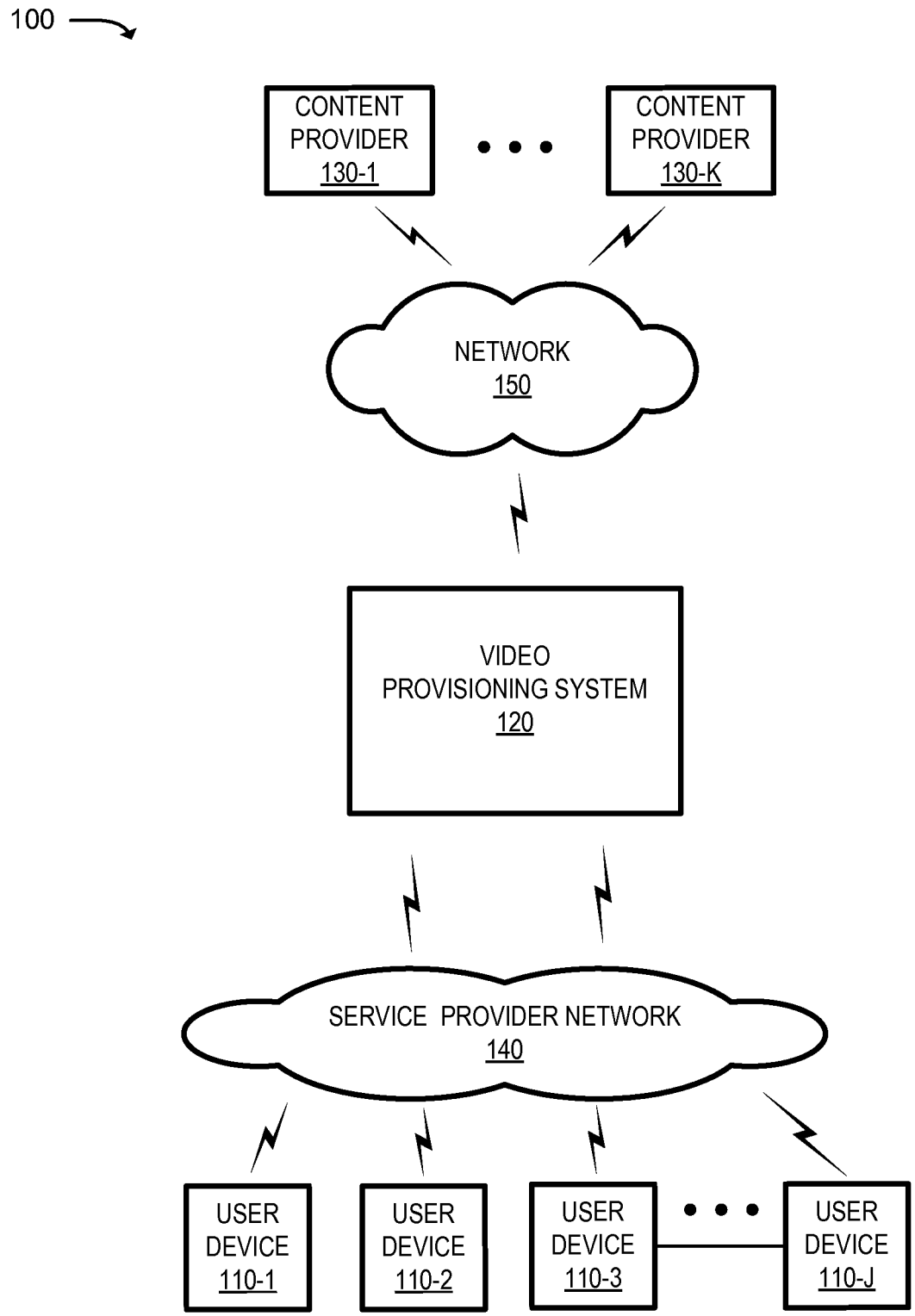
FIG. 1 is a diagram illustrating an example environment according to an implementation described herein.

The following detailed description refers to the accompanying drawings. The same reference numbers in different drawings identify the same or similar elements.

An implementation described herein may relate to a video provisioning system (VPS). The VPS may enable a customer to purchase and consume a video asset using different types of user devices, including a set top box, a computer device, and/or a wireless mobile device. Furthermore, the VPS may enable the customer to consume (e.g., view) the purchased video asset using any number of different devices registered with the VPS. For example, the customer may view the video asset on a non-set top box device, such as a personal computer or a wireless mobile device, using a dedicated client application or using a browser application. A customer may use a browsing application (e.g., Microsoft Explorer, Google Chrome, Apple Safari, Mozilla Firefox, etc.) when a dedicated client application has not been installed on the customer's device or when a dedicated client application may not be available for the customer's particular device.

An implementation described herein may relate to managing playback of a video asset, provided by the VPS, using a web browser application, where the video asset is encrypted using a first digital rights management (DRM) scheme and where a media player of the web browser application uses a second DRM scheme to authorize playback of the video asset. A license, associated with the second DRM scheme, may be generated based on DRM information associated with the first DRM scheme. The DRM information, associated with the first DRM scheme, may be stored in metadata associated with the video asset when the video asset is ingested by the VPS and stored in a catalog of video assets. The license, associated with the second DRM scheme, may be obtained by a user device from a license server using, for example, token based authentication. The license, associated with the second DRM scheme, may be used by a media player of a web browser application to decrypt the video asset. Thus, a video asset encrypted using the first DRM scheme may not need to be re-encrypted using a second DRM scheme in order to play the video asset with a media player that uses the second DRM scheme.

In one example, the video asset may be encrypted using Microsoft Windows Media® DRM (WMDRM) and a browser application may play video assets, purchased via the VPS, using a Microsoft Silverlight® media player that associated with a PlayReady® DRM scheme.

An implementation described herein may further relate to managing a bookmark, associated with a video asset, during playback of the video asset using a browser application. A bookmark, associated with a video asset, may define a first location of the video asset at which the customer stopped playing the video asset. For example, the bookmark may identify that the customer stopped playing the video asset at 30 minutes from the beginning of the video asset. The bookmark may be stored in a video asset library associated the customer's VPS profile. If the customer uses a browser application to play the video asset, the VPS may convert a first bookmark to a first range header value and if the customer stops playing the video asset, the VPS may convert a second range header value to a second bookmark and store the second bookmark in the customer's VPS profile. A range header value may be a value included in a range header field of a header of a Hypertext Transfer Protocol (HTTP) packet, where the range header value indicates an offset from a beginning of a resource associated with the HTTP packet. In one example, the range header value may be specified in terms of number of bytes.

The term video asset, as used herein, may include VOD content, pay-per-view (PPV) video content, rented video content, free television content (e.g., from free television broadcasters, etc.), paid for television content (e.g., from pay television content providers), on-line video content (e.g., on-line television programs, movies, videos, etc.), advertising, games, music videos, promotional information (e.g., such as previews, trailers, etc.), etc. A video asset may be stored in one or more video files that contain video information that can be played on a user device.

FIG. 1 is a diagram of an example environment in which the systems and/or methods, described herein, may be implemented. As shown in FIG. 1, environment 100 may include a group of user devices 110-1, ..., 110-J (where J≥1) (referred to herein collectively as "user devices 110" and individually as "user device 110"), a VPS 120, a group of content providers 130-1, ..., 130-K (where K≥1) (referred to herein collectively as "content providers 130" and individually as "content provider 130"), a service provider network 140, and a network 150. Devices, systems, and/or networks of environment 100 may interconnect via wired connections, wireless connections, or a combination of wired and wireless connections.

User device 110 may include a computation or communication device that is capable of communicating with service provider network 140. For example, user device 110 may include a radiotelephone, a personal communications system (PCS) terminal (e.g., that may combine a cellular radiotelephone with data processing and data communications capabilities), a personal digital assistant (PDA) (e.g., that can include a radiotelephone, a pager, Internet/intranet access, etc.), a laptop computer, a tablet computer, a set top box, a digital video recorder (DVR), a personal gaming system, a smart phone, and/or another type of computation or communication device.

User device 110 may communicate with VPS 120 and/or perform certain operations to obtain a video asset from VPS 120. For example, user device 110 may access a portal (e.g., a website, a user interface, an interactive program guide (IPG), an interactive media guide (IMG), etc.) associated with VPS 120, to browse, search, select, and/or obtain a video asset.

VPS 120 may include one or more devices that gather, process, search, store, and/or provide information in a manner similar to that described herein. VPS 120 may be capable of communicating with content providers 130 via network 150 and/or user devices 110 via service provider network 140. VPS 120 may provide a video provisioning service to user devices 110.

VPS 120 may, for example, perform operations associated with video content ingestion, processing, and/or distribution for one or more types of user devices 110, associated with a user, within environment 100. VPS 120 may communicate with one or more content providers 130 to acquire video content. VPS 120 may connect to a collection of various types user devices 110 associated with a user, such as, for example, a set top box, a computer device, a wireless handset device (e.g., a smart phone, a personal digital assistant (PDA), etc.), and/or other types of user devices 110. VPS 120 may connect to the set top box via a television service provider network 140 (e.g., a cable television network, a satellite television network, a fiber optic television network, or some combination thereof). VPS 120 may connect to the computer device via a broad band service provider network 140 (e.g., via the Internet). VPS 120 may connect to the wireless handset device via a wireless service provider network 140. VPS 120 may perform an ingestion operation on the acquired video content. VPS 120 may process and/or publish the ingested video content in a manner that allows the video content to be offered and/or distributed to the different types of user devices 110.

Content provider 130 may include any type or form of content provider. For example, content provider 130 may include free television broadcast providers (e.g., local broadcast providers, such as NBC, CBS, ABC, and/or Fox), for-pay television broadcast providers (e.g., TNT, ESPN, HBO, Cinemax, CNN, etc.), and/or Internet-based content providers (e.g., Youtube, Vimeo, Netflix, Hulu, Veoh, etc.) that stream content from web sites and/or permit content to be downloaded (e.g., via progressive download, etc.). Content provider 130 may include on-demand content providers (e.g., video on demand (VOD), pay per view (PPV), etc.). A media stream, as used herein, may refer to a stream of content that includes video content (e.g., a video stream), audio content (e.g., an audio stream), and/or textual content (e.g., a textual stream).

Service provider network 140 may include one or more wired and/or wireless networks via which user devices 110 communicate with and/or receive video content from VPS 120. For example, service provider network 140 may include a cellular network, the Public Land Mobile Network (PLMN), a second generation (2G) network, a third generation (3G) network, a fourth generation (4G) network (e.g., a long term evolution (LTE) network), a fifth generation (5G) network, and/or another network. Additionally, or alternatively, service provider network 140 may include a code division multiple access (CDMA) network, a global system for mobile communications (GSM) network, a general packet radio services (GPRS) network, or a combination of CDMA, GSM, and/or GPRS networks. Additionally, or alternatively, service provider network 140 may include a wide area network (WAN), a metropolitan area network (MAN), an ad hoc network, an intranet, a fiber optic-based network (e.g., a fiber optic service (FiOS) network), a television network, and/or a combination of these or other types of networks.

Network 150 may include one or more wired and/or wireless networks. For example, network 150 may include a cellular network, the PLMN, a 2G network, a 3G network, a 4G network (e.g., an LTE network), a 5G network, and/or another network. Additionally, or alternatively, network 150 may include a WAN, a MAN, a telephone network (e.g., the Public Switched Telephone Network (PSTN)), an ad hoc network, an intranet, the Internet, a fiber optic-based network, and/or a combination of these or other types of networks.

Although FIG. 1 shows example components of environment 100, in other implementations, environment 100 may include fewer components, different components, differently arranged components, or additional components than depicted in FIG. 1. Additionally or alternatively, one or more components of environment 100 may perform functions described as being performed by one or more other components of environment 100.

Figure 2:
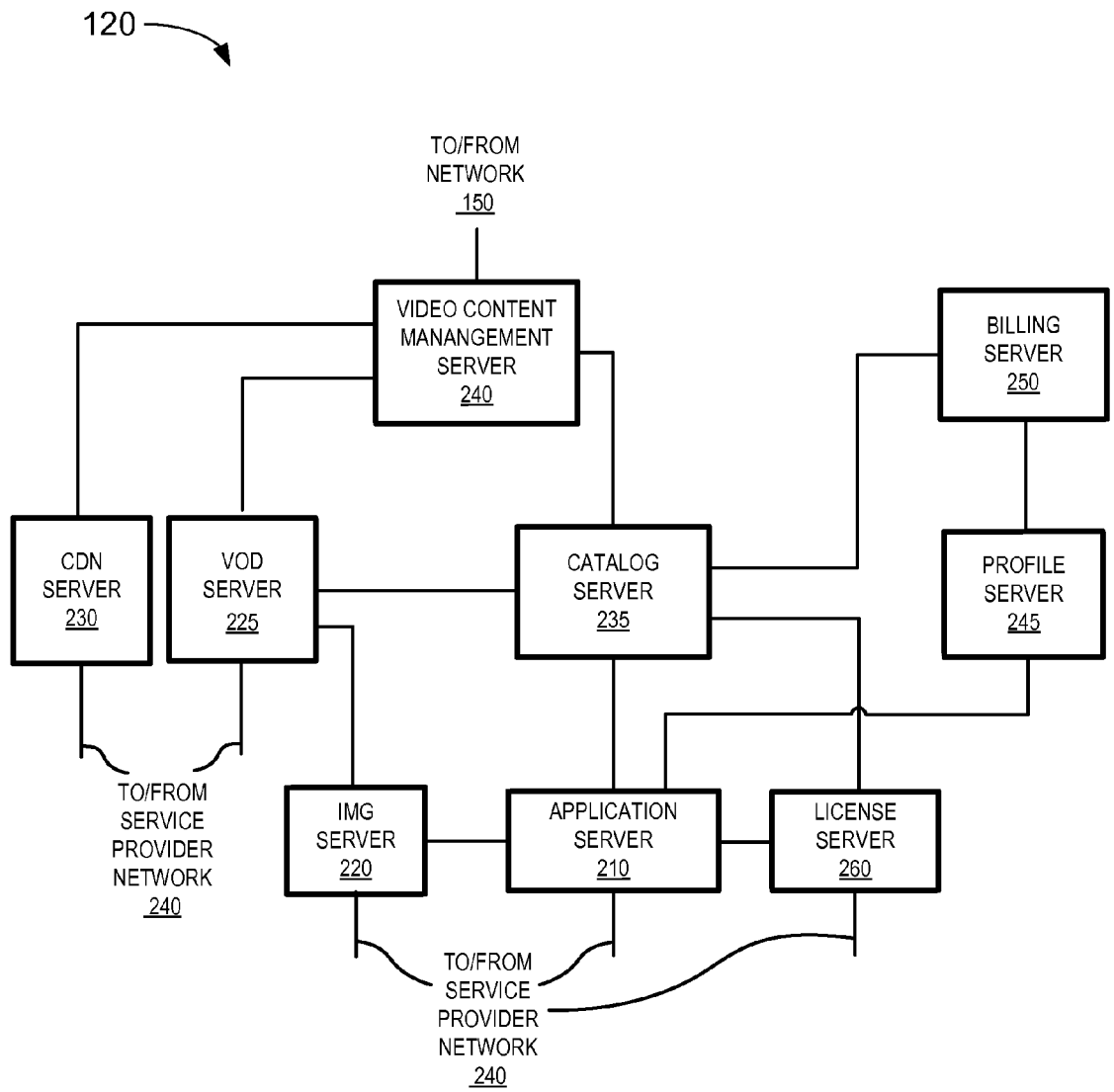
FIG. 2 is a diagram illustrating example components associated with the video provisioning system of FIG. 1.

FIG. 2 is a diagram of example devices associated with VPS 120. As shown in FIG. 2, VPS 120 may include an application server 210, an interactive media guide (IMG) server 220, a video on-demand (VOD) server 225, a content delivery network (CDN) server 230, a catalog server 235, a video content management (VCM) server 240, a profile server 245, a billing server 250, and a license server 260.

In the description below, VOD server 225 is described as provisioning video services for a type of user device 110 (i.e., a set top box) and CDN server 230 is described as provisioning video services for another type of user device 110 (i.e., a computer device, a wireless handset device, etc.) for explanatory purposes. In another implementation, the video services may be provisioned for the set top box and/or the other types of user devices 110 in a number of ways. For example, VOD server 225 and/or CDN server 230 may be combined into a single device that provisions the video services for each type of user device 110. In another example, the video services may be provisioned, for each type of user device 110, by another device and/or network instead of, or in combination with, VOD server 225 and/or CDN server 230. Additionally, IMG server 220 is described as providing an a store front portal (i.e., via an IMG), that can be accessed by the set top box, and application server 210 is described as providing another store front portal (e.g., via a web page, a user interface, an interactive program guide, etc.), that can be accessed by the other types of user devices 110, for explanatory purposes. In another implementation, the store front portal may be provisioned for the set top box and/or the other types of user devices 110 in a number of ways. For example, IMG server 220 and/or application server 210 may be combined into a single device that provisions the store front portal for each type of user device 110. In another example, the store front portal may be provisioned, for each type of user device 110, by another device and/or network instead of, or in combination with, IMG server 220 and/or application server 210. Thus, the examples below are provided for explanatory purposes only.

Application server 210 may include one or more server devices, or other types of computation or communication devices, that gather, process, search, store, and/or provide information in a manner similar to that described herein. Application server 210 may receive metadata that has been published by catalog server 235.

Metadata may enable the video assets to be identified, managed, offered, and/or distributed to a user device. The metadata may, for example, include an identifier associated with a video asset (e.g., a number, a name, a title, etc.); a genre of the video asset (e.g., horror, comedy, adult, etc.); a category of the video asset (e.g., VOD asset, a PPV asset, an on-line asset, etc.); a text description, a key word index, and/or summary of the video asset; an image (e.g., cover art) associated with the video asset, and/or information associated with artists associated with the video asset (e.g., names of actors, directors, producers, etc.). The metadata may also, or alternatively, include information associated with a type of video asset (e.g., a movie, music video, a game, etc.); a rating associated with the video asset (e.g., general audience (G), parental guidance (PG), PG-13, restricted (R), mature audience (MA), etc.); user reviews associated with the video asset; a price associated with the video asset (e.g., a sale price, a rental price per day, a pay-per-view price, etc.); and/or an availability period associated with the video asset (e.g., release dates, restriction periods, blackout periods, etc.). The metadata may also, or alternatively, include information associated with a storage location (e.g., a uniform resource locator (URL)) corresponding to the video asset; a format associated with the video asset (e.g., a resolution level, compression/decompression (CODEC) information, a screen size, a frame size, a frame refresh rate, a bit rate, etc.); and/or types of user devices supported by each format, etc.

The metadata may be associated with video assets that are to be made available and/or offered (e.g., for sale, rent, subscription, etc.) to user devices 110. Application server 210 may host a portal (e.g., a VPS store front), such as a private website (e.g., for subscribing user devices 110), a public website (e.g., for non-subscribing user devices 110), a user interface (UI) (e.g., that is accessible by wireless handset user devices 110, etc.), an interactive program guide (e.g., an IMG for set top box-type user devices 110) and/or other types of user interfaces. The portal may enable SSO portal access, to a user of one or more user devices 110, based on the same login credentials (e.g., username, password, personal identification number (PIN), etc.). Application server 210 may publish all or a portion of the metadata to the portal that permits any of user devices 110 to browse, perform searches, process payment, etc. for video assets based on the metadata that is published to the portal.

Application server 210 may store information associated with a transaction history that corresponds to a type of user device 110 (e.g., a computer user device 110, a wireless handheld user device 110, a gaming user device 110, etc.) that is different than a set top box user device 110. The transaction history may include information regarding prior transactions (e.g., purchases, rentals, subscriptions, etc.), associated with one or more video assets, by user device 110. The transaction history may also identify a period of time during which a rental period or subscription period, for a video asset, is valid. Application server 210 may, in another example, transmit information, associated with the transaction history, to profile server 260, to be stored in a user profile associated with a user of user device 110.

IMG server 220 may include one or more server devices, or other types of computation or communication devices, that gather, process, search, store, and/or provide information in a manner similar to that described herein. IMG server 220 may, for example, process metadata, that has been published by catalog server 235 and/or VOD server 225, in a manner similar to that described above (e.g., with respect to application server 210). The metadata may be associated with video content that may be obtained by a particular type of user device 110, such as a set top box user device 110.

IMG server 220 may publish all or a portion of the metadata to an IMG UI that the set top box user device 110, associated with the user, may render for display on a video display device. IMG server 220 may permit the set top box user device 110 to access information associated with video assets, stored by VOD server 225, and access the actual video assets. IMG server 220 may, in another example implementation, communicate with application server 210, which may permit the set top box user device 110 to access the metadata associated video assets that are stored in CDN server 230.

IMG server 220 may store information associated with a transaction history that corresponds to a set top box user device 110. The transaction history may include information regarding prior transactions (e.g., purchases, rentals, subscriptions, etc.), associated with one or more video assets, by set top box user device 110. The transaction history may also identify a period of time during which a rental period or subscription period, for a video asset, is valid. Application server 210 may, in another example, transmit information, associated with the transaction history, to profile server 260, to be stored in a user profile associated with a user of user device 110.

VOD server 225 may include one or more server devices, or other types of computation or communication devices, that gather, process, search, store, and/or provide information in a manner similar to that described herein. VOD server 225 may, for example, perform operations to receive, store, process, and/or distribute video content in a format that is supported by set top box user devices 110.

VOD server 225 may receive published video assets and/or metadata from VCM server 240. VOD server 225 may store the published video assets in a memory associated with VOD server 225. VOD server 225 may publish a portion of the metadata, associated with video assets (e.g., that are available for release and/or not subject to a blackout, etc.), to IMG server 220. In another example implementation, VOD server 225 may communicate with content provider 130 to receive video content directly from content provider 130 (e.g., not via VCM server 240).

CDN server 230 may include one or more server devices, or other types of computation or communication devices, that gather, process, search, store, and/or provide information in a manner similar to that described herein. CDN server 230 may, for example, perform operations to receive, store, process, and/or distribute video content in a format that is supported by one or more types of user devices 110 (e.g., a computer device, a wireless mobile device, a gaming device, etc.) other than, or in addition to, a set top box user device 110. CDN server 230 may actually represent a content delivery network that includes multiple routing and/or storage devices.

CDN server 230 may receive published video assets in multiple video formats from VCM server 240. CDN server 230 may store the published video assets in a memory associated with CDN server 230. CDN server 230 may identify a respective storage location and/or URL for each format of each video asset that are stored within the memory and may send information associated with the storage locations and/or the URLs to catalog server 235. CDN server 230 may provide video assets to wireless handset user devices 110 via a wireless service provider network 140. CDN server 230 may provide the video assets to a computer user device 110 via a broadband service provider network 140 (e.g., the Internet). In another example implementation, CDN server 230 may provide the video assets to a set top box user device 110 via a television service provider network 140 and/or via VOD server 225.

Catalog server 235 may include one or more server devices, or other types of computation or communication devices, that gather, process, search, store, and/or provide information in a manner similar to that described herein. Catalog server 235 may, for example, receive, from VCM server 240, published metadata associated with video assets that have been published to VOD server 225 and/or CDN server 230. Catalog server 235 may identify, from the metadata, information associated with the availability of the video assets based on dates on which the video assets are released, blacked out, etc. Catalog server 235 may process and/or package the metadata in order to offer, to user devices 110, the video assets to which the metadata corresponds. The processed metadata, associated with the video assets, may include identifiers (e.g., video asset numbers, titles, etc.), prices (e.g., sale prices, rental prices, subscription prices, etc.), descriptions (e.g., a synopsis, a summary, etc. of the video assets), ratings, reviews, genres, casting information (e.g., actors, directors, producers, etc.), etc. Catalog server 235 may, for example, publish the metadata to the store front portal associated with VPS application server 210. Catalog server 235 may not publish metadata associated with video assets that are identified as not yet being available.

VCM server 240 may include one or more server devices, or other types of computation or communication devices, that gather, process, search, store, and/or provide information in a manner similar to that described herein. VCM server 240 may, for example, communicate with content providers 130 to ingest video assets to be processed by VPS 120. VCM server 240 may process the video assets to generate copies of the video assets in one or more formats that are supported (e.g., that can be received, processed, and/or played) by the different types of user devices 210. VCM server 240 may publish the one or more formats, associated with the processed video assets, to VOD server 225 and/or CDN server 230.

VCM server 240 may also ingest, process, and/or publish metadata associated with the video assets. VCM server 240 may process the metadata to ensure that the metadata is supported by the different types of user devices 210. VCM server 240 may publish the processed metadata to catalog server 235. The metadata may include DRM information. For example, a video asset may be encrypted using a first DRM scheme (e.g., a WMDRM scheme) and the metadata may include a key associated with the first DRM scheme. The key, associated with the first DRM scheme, may be used by license server 260 as a license seed to generate a license associated with a second DRM scheme (e.g., a PlayReady DRM scheme).

Profile server 245 may include one or more server devices, or other types of computation or communication devices, that gather, process, search, store, and/or provide information in a manner similar to that described herein. Profile server 245 may, for example, store information associated with a profile that includes information regarding the user and each user device 110 with which the user has registered with VPS 120. For example, information associated with the profile may further include information associated with the user (e.g., a username, password, PIN, etc.), information associated with each user device 110, such as a respective identifier (e.g., a mobile directory number (MDN), an Internet protocol (IP) address, a media access control (MAC) address, a CODEC identifier, etc.), and/or information associated with a type of user device 110, such as a computer device (e.g., a lap top computer, a tablet computer, etc.), a wireless mobile device (e.g., a Droid®, a Blackberry®, an iPhone®, etc.), a set top box, a gaming device, etc.

The information associated with the profile may also include a respective user history (e.g., prior purchases, prior URLs accessed, prior downloads, bookmarks associated with purchased video assets, etc.) associated with each user device 110; information associated with services for which user device 110 has subscribed; information associated with a location (e.g., an address, a zip code, a city, etc.) of the user and/or user device 110; information associated user account limits, restrictions, etc.; information associated with a language spoken by the user; etc.

Billing server 250 may include one or more server devices, or other types of computation or communication devices, that gather, process, search, store, and/or provide information in a manner similar to that described herein. Billing server 250 may, for example, perform billing operations associated with accounts that correspond to each user device 110 associated with a user. For example, billing server 250 may receive an indication that user device 110 (e.g., a computer device), associated with the user, downloaded a video asset (e.g., via a broadband service associated with service provider network 140) as a result of a transaction via the store front portal. Billing server 250 may generate billing information that identifies the video asset, the type of transaction (e.g., a purchase, rental, subscription, etc.), a price associated with the transaction, a time at which the transaction occurred, etc. Billing server 250 may associate the billing information with an account that corresponds to the user and/or user device 110. Billing server 250 may generate other billing information regarding another transaction with another user device 110 (e.g., a set top box) with which the user is associated. Billing server 250 may associate the other billing information with another account that corresponds to the user and/or the other user device 110. In yet another example, billing server 250 may process payment information (e.g., based on credit card information, debit card information, etc.) associated with a transaction with a further user device 110 to purchase, rent, subscribe to, etc. another video asset.

License server 260 may include one or more server devices, or other types of computation or communication devices, that gather, process, search, store, and/or provide information in a manner similar to that described herein. For example, license server 260 may generate a license, associated with a second DRM scheme, and provide the license to a media player in connection with a video asset. The media player may use the license to decrypt the video asset. License server 260 may generate the license, associated with the second DRM scheme, based on information associated with a first DRM scheme. For example, license server 260 may use a key, associated with the first DRM scheme, as a license seed to generate the license, associated with the second DRM scheme. In one example, license server 260 may correspond to a Microsoft PlayReady license server.

Although FIG. 2 shows example components of VPS 120, in other implementations, VPS 120 may include fewer components, different components, differently arranged components, or additional components than depicted in FIG. 2. Additionally or alternatively, one or more components of VPS 120 may perform functions described as being performed by one or more other components of VPS 120.

Figure 3:
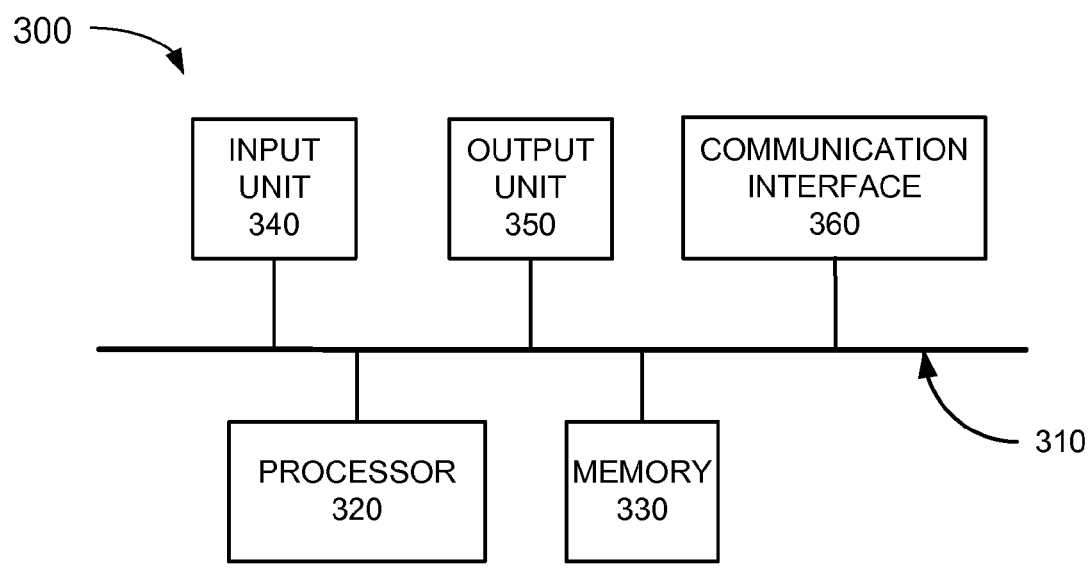
FIG. 3 is a diagram illustrating example components of a device that corresponds to one or more of the components of FIG. 2.

FIG. 3 is a diagram of example components of a device 300 that may correspond to user device 110, content provider 130, application server 210, IMG server 220, VOD server 225, CDN server 230, catalog server 235, VCM server 240, profile server 245, billing server 250, and/or license server 260. Alternatively, each of user device 110, content provider 130, application server 210, IMG server 220, VOD server 225, CDN server 230, catalog server 235, VCM server 240, profile server 245, billing server 250, and/or license server 260 may include one or more devices 300.

As shown in FIG. 3, device 300 may include a bus 310, a processor 320, a memory 330, an input unit 340, an output unit 350, and a communication interface 360. Bus 310 may include a path that permits communication among the components of device 300. Processor 320 may include a single-core processor, multi-core processor, microprocessor, and/or processing logic that may interpret and execute instructions. Memory 330 may include any type of dynamic storage device that may store information and instructions, for execution by processor 320, and/or any type of non-volatile storage device that may store information for use by processor 320.

Input unit 340 may include a mechanism that permits a user to input information to device 300, such as a keyboard, a keypad, a button, a switch, etc. Output unit 350 may include a mechanism that outputs information to the user, such as a display, a speaker, one or more light emitting diodes (LEDs), etc. Communication interface 360 may include any transceiver-like mechanism that enables device 300 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. For example, communication interface 360 may include mechanisms for communicating with another device or system via a network, such as service provider network 140 and/or network 150. In one alternative implementation, communication interface 360 may be a logical component that includes input and output ports, input and output systems, and/or other input and output components that facilitate the transmission of data to other devices.

As will be described in detail below, device 300 may perform certain operations relating to managing consumption of a video asset, based on multiple digital rights management schemes, for a video provisioning system. Device 300 may perform these operations in response to processor 320 executing software instructions contained in a computer-readable medium, such as memory 330. A computer-readable medium may be defined as a non-transitory memory device. A memory device may include space within a single physical memory device or spread across multiple physical memory devices. The software instructions may be read into memory 330 from another computer-readable medium or from another device. The software instructions contained in memory 330 may cause processor 320 to perform processes described herein. Alternatively, hardwired circuitry may be used in place of or in combination with software instructions to implement processes described herein. Thus, implementations described herein are not limited to any specific combination of hardware circuitry and software.

Although FIG. 3 shows example components of device 300, in other implementations, VPS 120 may include fewer components, different components, differently arranged components, or additional components than depicted in FIG. 3. Additionally or alternatively, one or more components of device 300 may perform functions described as being performed by one or more other components of device 300.

Figure 4:
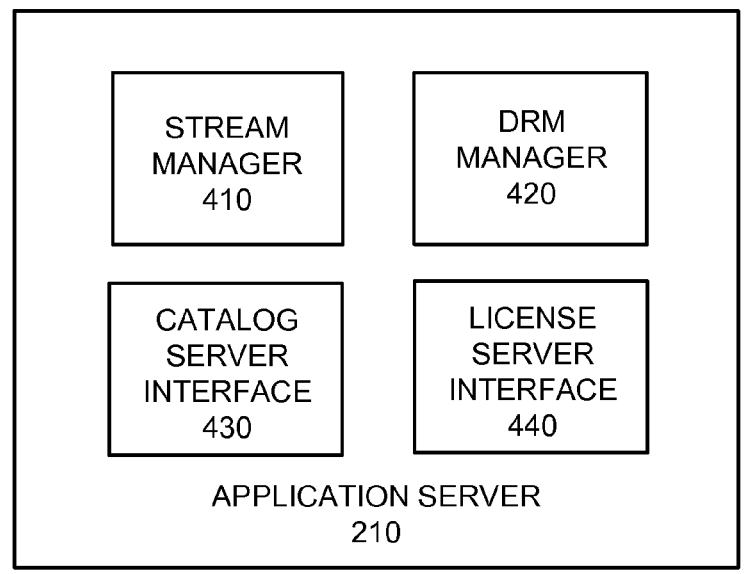
FIG. 4 is a diagram of example functional components of the application server of FIG. 2.

FIG. 4 is a diagram of example functional components of application server 210. As shown in FIG. 4, application server 210 may include a stream manager 410, a DRM manager 420, a catalog server interface 430, and a license server interface 440.

Stream manager 410 may authorize a particular stream of a video asset for a user. A user may be authorized to stream a particular number of video assets at a time in connection with the user's registered devices. For example, a user may be authorized for one stream for all user devices other than a set top box. Thus, if no user devices, other than a set top box, registered with the user's VPS account, are currently receiving a stream of a video asset, stream manager 410 may authorize a stream in response to receiving a request to stream a video asset.

DRM manager 420 may implement token based authentication for providing a DRM license to user device 110. For example, DRM manager 420 may provide a DRM token to a media player, of user device 110, and the media player may use the DRM token to obtain a DRM license from license server 260. Furthermore, DRM manager 420 may authorize license server 260 to issue a DRM license if the DRM license was requested with a valid DRM token.

Catalog server interface 430 may interact with catalog server 235. For example, catalog server interface 430 may obtain a URL associated with a video asset from catalog server 235 and the URL may be provided to a browser application associated with user device 110. As another example, catalog server interface 430 may receive video asset information from catalog server 235 and may format the information into a format compatible with application server 210. For example, catalog unit 430 may format the information into frames for a store front web page.

License server interface 440 may interface license server 260 with DRM manager 420. For example, license server interface 440 may receive a request from license server 260 to issue a DRM license for a video asset, may transform the request into a format compatible with DRM manager 420, and may forward the request to DRM manager 420. Moreover, license server interface 440 may receive an authorization to issue a DRM license from DRM manager 420, may convert the authorization into a format compatible with license server 260, and may forward the authorization to license server 260.

Although FIG. 4 shows example functional components of application server 210, in other implementations, application server 210 may include fewer functional components, different functional components, differently arranged functional components, or additional functional components than depicted in FIG. 4. Additionally or alternatively, one or more functional components of application server 210 may perform functions described as being performed by one or more other functional components of application server 210.

Figure 5:
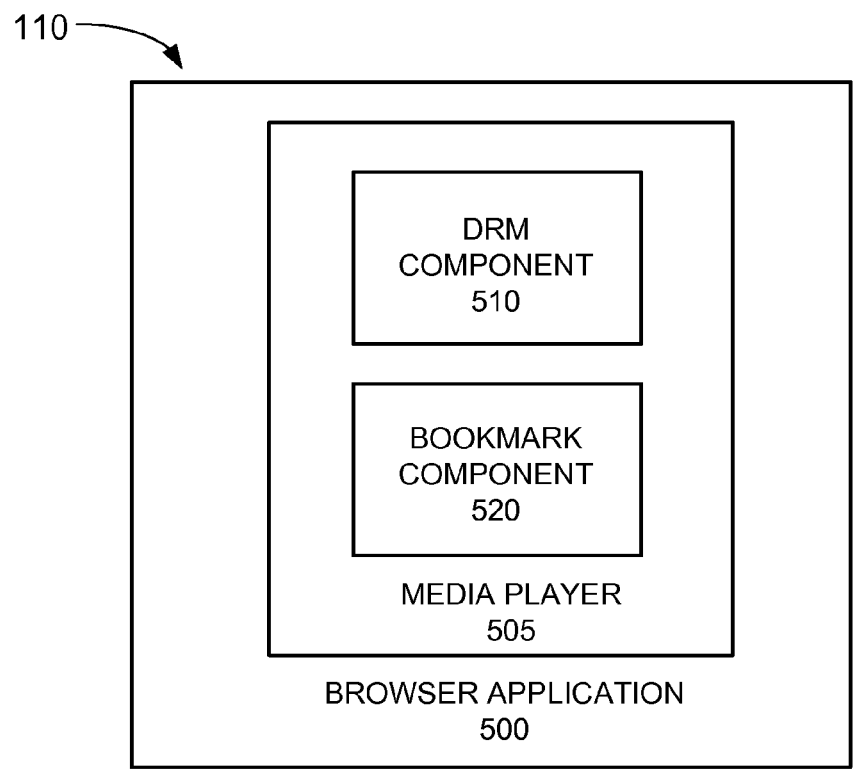
FIG. 5 is a diagram of example functional components of the user device of FIG. 1.

FIG. 5 is a diagram of example functional components of user device 110. As shown in FIG. 5, user device 110 may include a browser application 500. Browser application 500 may include a software application (e.g., Microsoft Explorer, Google Chrome, Apple Safari, Mozilla Firefox, etc.) for retrieving, presenting, and/or traversing resources on the World Wide Web. Browser application 500 may include a media player 505. Media player 505 may include an add-on or plug-in application for playing back multimedia files, such as video and/or audio files. In one example, media player 505 may include a Microsoft Silverlight player. Media player 505 may include a DRM component 510 and a bookmark component 520.

DRM component 510 may be associated with a particular DRM scheme. DRM component 510 may request a DRM token from application server 210, may use the DRM token to request a DRM license, associated with the particular DRM scheme, from license server 260, and may decrypt video assets using the DRM license.

Bookmark component 520 may receive a bookmark in connection with a video asset and may initiate playback of the video asset at a location specified by the bookmark. For example, bookmark component 520 may receive a range header value and may initiate retrieval of the video asset file at the range header value.

Although FIG. 5 shows example functional components of user device 110, in other implementations, user device 110 may include fewer functional components, different functional components, differently arranged functional components, or additional functional components than depicted in FIG. 5. Additionally or alternatively, one or more functional components of user device 110 may perform functions described as being performed by one or more other functional components of user device 110.

Figure 6:
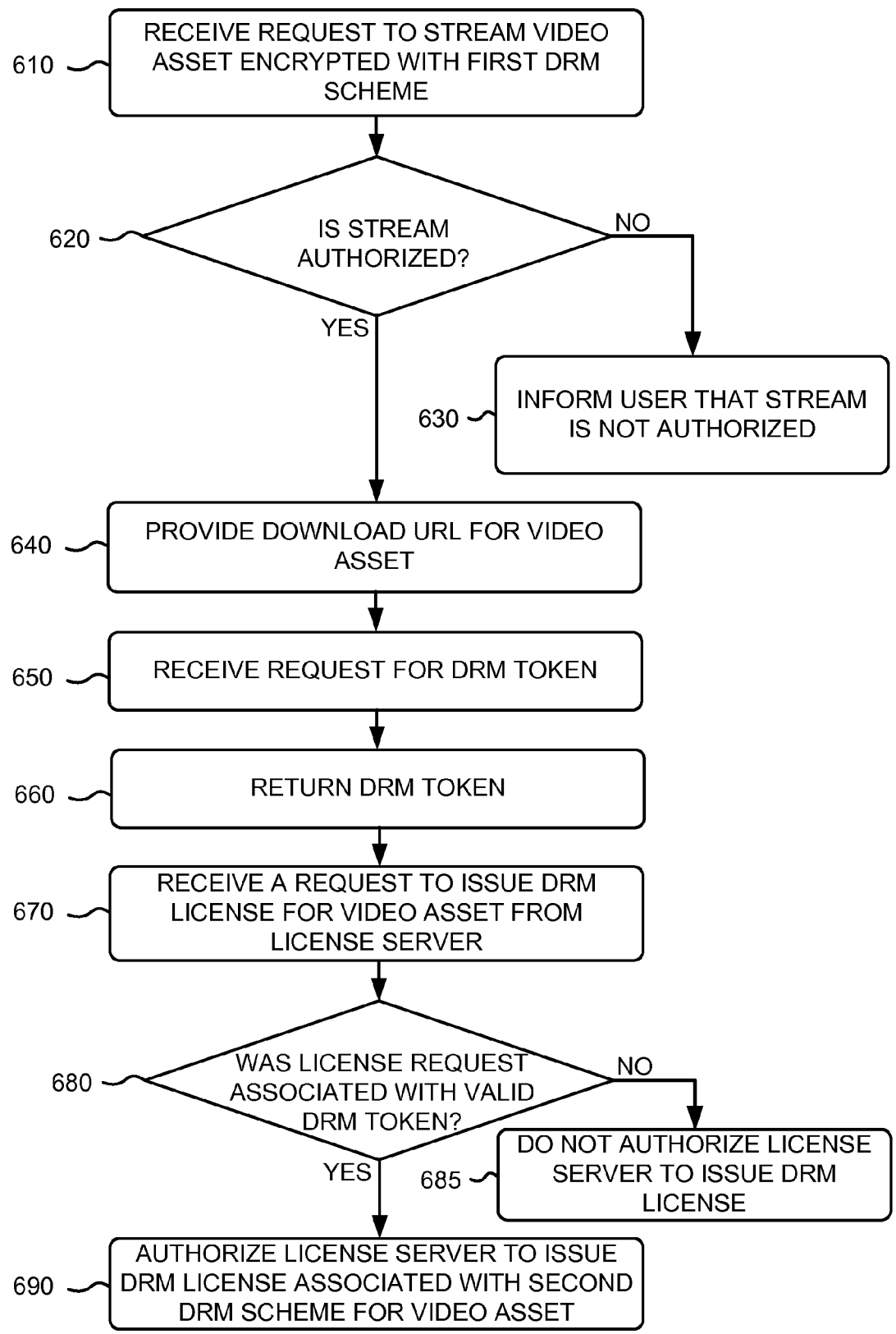
FIG. 6 is a flow chart of an example process for managing consumption of a video asset based on multiple digital rights management schemes according to an implementation described herein.

FIG. 6 is a flow chart of an example process for managing consumption of a video asset based on multiple digital rights management schemes. In one implementation, the process of FIG. 6 may be performed by VPS 120. In other implementations, some or all of the process of FIG. 6 may be performed by another device or a group of devices separate from VPS 120 and/or including VPS 120.

The process of FIG. 6 may include receiving a request to stream a video asset encrypted using a first DRM scheme (block 610). For example, a user may purchase a video asset and information about the video asset may be stored in the user's library in the user's profile stored in profile server 245. The user may access the library of purchased video assets and may request to consume a purchased video asset. For example, the user may navigate to a web page that displays the user's library of purchased video assets using browser application 500 and may click a "watch now" button associated with a video asset that the user has purchased.

A determination may be made as to whether a stream is authorized (block 620). For example, stream manager 410 may determine whether to authorize streaming of the video asset by determining how many streams are currently associated with devices registered with the user and determining whether the number of stream is less than a maximum allowed number of streams. In one example, information about the number of current streams associated with the user's profile may be stored by stream manager 410 in a memory associated with application server 210. In another example, the information about the number of current streams associated with the user's profile may be stored in the user's profile in a memory associated with profile server 245.

If it is determined that the stream is not authorized (block 620-NO), the user may be informed that the stream is not authorized (block 630). For example, stream manager 410 may send a message to user device 110, informing the user that the maximum number of available streams has been reached and that an additional stream is not authorized. In one example, if the user profile is associated with a maximum number of available streams, stream manager 410 may inform the user that the streaming of the video asset is not available. In another example, if the user profile is associated with a maximum number of available streams, stream manager 410 may terminate another stream (e.g., an oldest stream) associated with the user's profile before authorizing streaming of the requested video asset.

If it is determined that the stream is authorized (block 620-YES), a download URL for the video asset may be provided (block 640). For example, application server 210 may retrieve a URL associated with the requested video asset from a record associated with the video asset and stored in catalog server 235. Application server 210 may provide the retrieved URL to browser application 500 of user device 110.

A request may be received for a DRM token (block 650) and a DRM token may be returned (block 660). For example, user device 110 may determine that the retrieved URL is associated with a DRM file that may need to be decrypted and may, in response, request a DRM token from application server 210. The request may include authentication credentials associated with the user. For example, the request may include a username and password associated with the user. Application server 210 may authenticate the user based on the received authentication credentials and, if the user is successfully authenticated, may generate a DRM token valid for a particular length of time (e.g., 60 seconds) and provide the generated DRM token to user device 110. The DRM token may enable user device 110 to request a DRM license for the requested video asset.

A request may be received to issue a DRM license for the video asset from a license server (block 670). For example, application server 210 may receive a request from license server 260 for an authorization to issue a DMR license, associated with a second DRM scheme, for the video asset encrypted using a first DRM scheme. For example, license server 260 may request authorization to issue a PlayReady license or another similar type of license.

A determination may be made as to whether the license authorization request is associated with a valid DRM token (block 680). For example, the license authorization request may include a DRM token associated with the license request and DRM manager 410 may determine whether the DRM token is a valid token by comparing the received DRM token with the DRM token provided to user device 110. Furthermore, DRM manager 410 may make sure that the DRM token has not expired. For example, DRM manager 410 may compare a time stamp included in the license authorization request with a time stamp associated with the issued DRM token to determine whether the DRM token is still valid or whether the DRM token has expired. If the DRM token has expired, DRM manager 410 may not authorize the issuing of the license.

If it is determined that the license request is not associated with a valid DRM token (block 680-NO), the license server may not be authorized to issue a DRM license (block 685). For example, application server 210 may send an indication to license server 260 that a DRM license should not be issued for the video asset. If it is determined that the license request is associated with a valid DRM token (block 680-YES), the license server may be authorized to issue a DRM license, associated with a second DRM scheme, for the video asset. For example, application server 210 may send an authorization to license server 260 to issue the DRM license (e.g., a PlayReady license).

Figure 7:
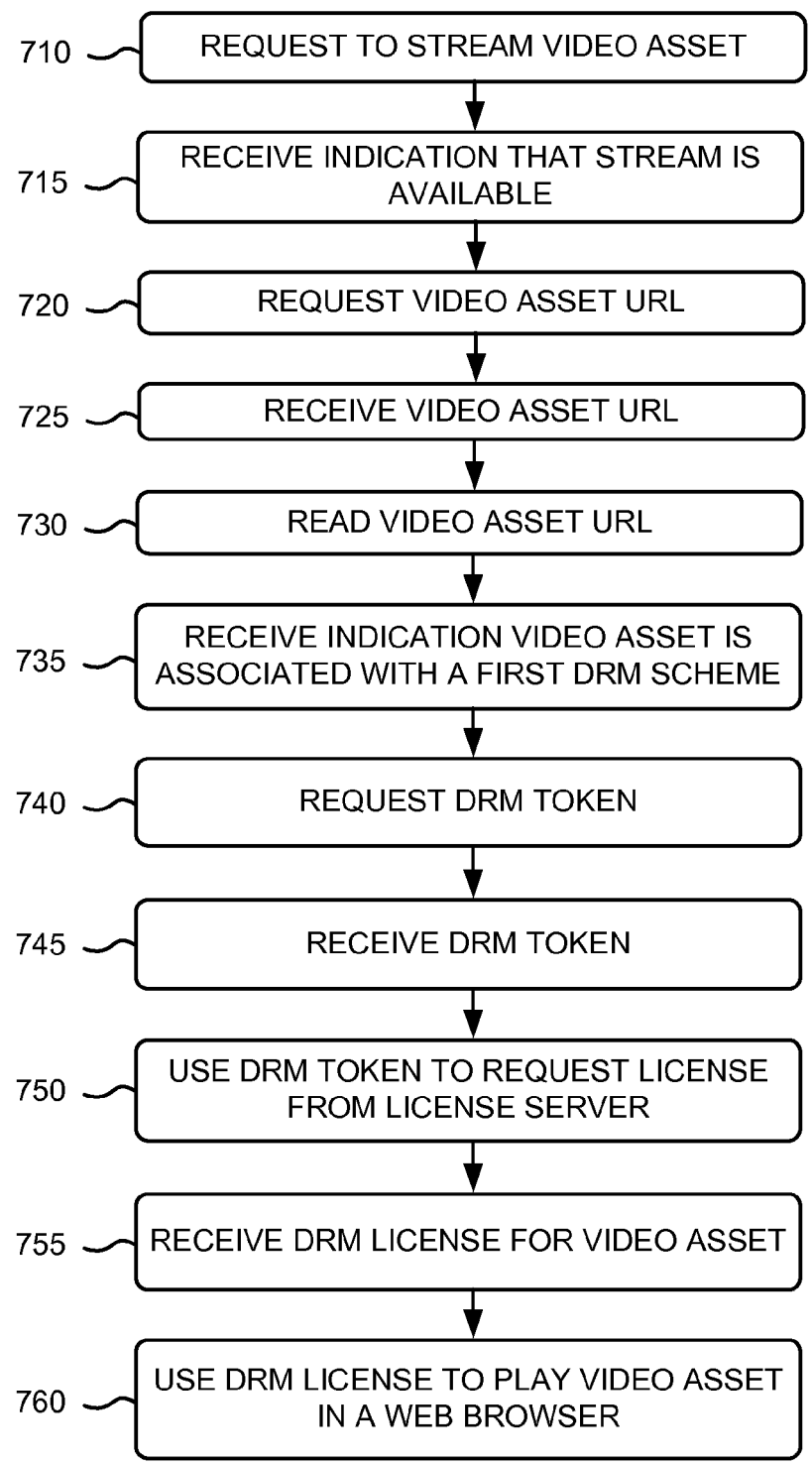
FIG. 7 is a flow chart of an example process for playback of a video asset based on multiple digital rights management schemes according to an implementation described herein.

FIG. 7 is a flow chart of an example process for playback of a video asset based on multiple digital rights management schemes. In one implementation, the process of FIG. 7 may be performed by user device 110. In other implementations, some or all of the process of FIG. 7 may be performed by another device or a group of devices separate from user device 110 and/or including user device 110.

The process of FIG. 7 may include requesting to stream a video asset (block 710) and an indication may be received that a stream is available (block 715). For example, browser application 500 may send a request to stream a video asset to application server 210 in response to a user selecting a selection object associated with playback of a purchased video asset. For example, the user may navigate to a web page that displays the user's library of purchased video assets using browser application 500 and may click a "watch now" button associated with a video asset that the user has purchased. Browser application 500 may receive an indication from application server 210 that the stream is authorized by application server 210.

A video asset URL may be requested (block 720) and the video asset URL may be received (block 725). For example, in response to receiving an indication that the stream is authorized, browser application 500 may request a URL associated with the video asset from application server 210 and may receive the requested URL. The URL may be associated with CDN server 230.

A video asset URL may be read (block 730). For example, browser application 500 may attempt to retrieve the video asset by contacting CDN server 230 to access the received URL. An indication may be received that the video asset is associated with a first DRM scheme (block 735). For example, browser application 500 may receive an indication from CDN server 230 that the URL is associated with a DRM resource.

A DRM token may be requested (block 740) and the DRM token may be received (block 745). For example, DRM component 510 of media player 505 may request a DRM token from application server 210 by sending a request for a DRM token. The request may include information identifying a particular video asset (e.g., a video asset identifier, a vide asset name, a URL associated with the video asset, etc.) and information identifying a user requesting the DRM token (e.g., username and password). In one example, the username and password may be retrieved by media player 505 from a stored location (e.g., the user may have selected to save the username and password in a cache associated with browser application 550 during a previous authentication process). In another example, media player 505 may prompt the user to enter the username and password prior to sending the request for the DRM token. Media player 505 may request a DRM token from application server 210 in response to sending the request. The DRM token may be valid for a particular length of time (e.g., for 60 seconds from the time the DRM token was issued by application server 210).

The DRM token may be used to request a license from a license server (block 750). For example, DRM component 510 of media player 505 may send a request to license server 260 to request a DRM license for the requested video asset. The request for the DRM license may include the received DRM token. License server 260 may use the DRM token to request authorization from application server 210 to issue a DRM license for the video asset.

A DRM license may be received for the video asset (block 755) and the DRM license may be used to play the video asset in a web browser (block 760). For example, DRM component 510 may receive a DRM license from license server 260 and may use the DRM license to decrypt the video asset file as the video asset file is received from CDN server 230. For example, media player 505 may correspond to a Microsoft Silverlight player and the DRM license may correspond to a PlayReady license. The PlayReady license may be used by the Silverlight player to decrypt a movie that was encrypted using WMDRM, as the PlayReady license may have been generated by license server 260 based on a WMDRM key associated with the video asset.

Media player 505 may playback the video asset using a progressive download method. For example, media player 505 may download a portion of the video asset file, may decrypt the portion, and may initiate playback of the decrypted portion while a next portion of the video asset file is being downloaded. Thus, obtaining the DRM license and using a progressive download method may not require the use of streaming servers.

Figure 8:
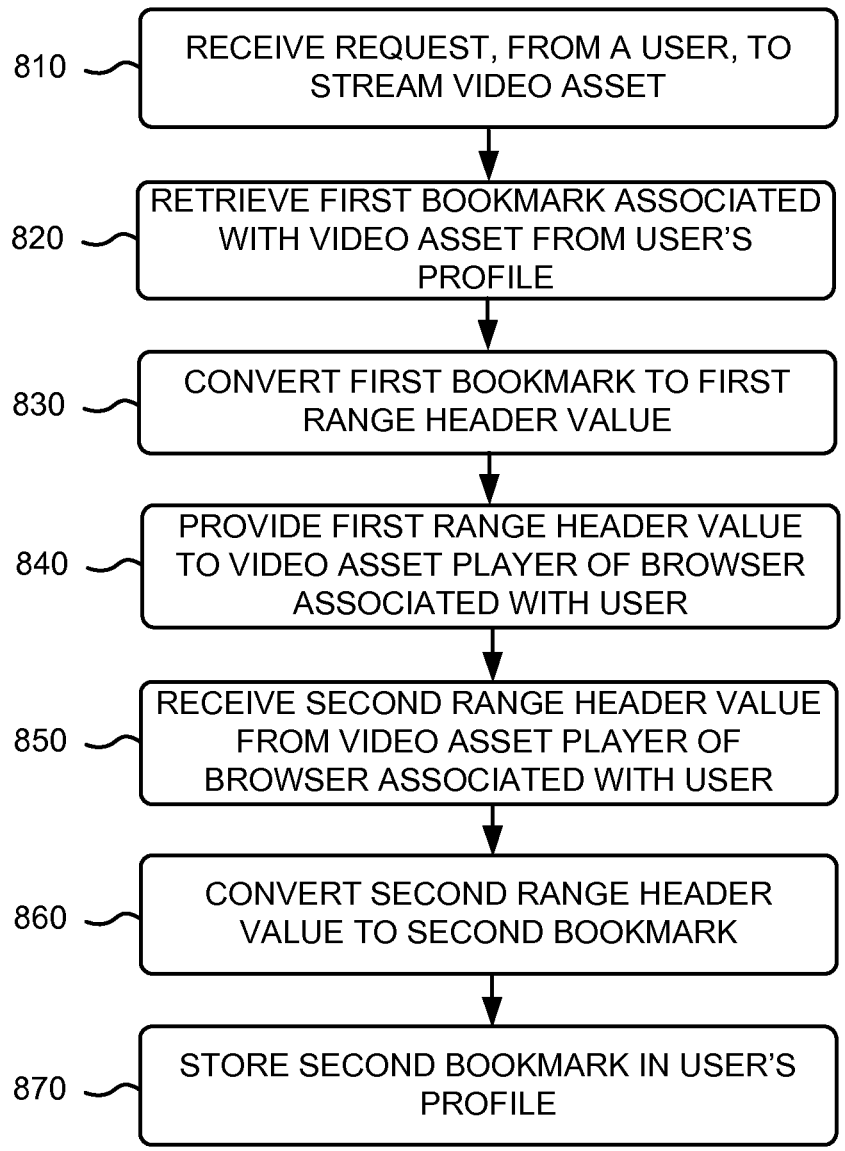
FIG. 8 is a flow chart of an example process for providing a bookmark to a user device according to an implementation described herein.

FIG. 8 is a flow chart of an example process for providing a bookmark to a user device. In one implementation, the process of FIG. 8 may be performed by VPS 120. For example, some or all of the process of FIG. 8 may be performed by application server 210. As another example, some or all of the process of FIG. 8 may be performed by CDN server 230. In other implementations, some or all of the process of FIG. 8 may be performed by another device or a group of devices separate from VPS 120 and/or including VPS 120.

The process of FIG. 8 may include receiving a request, from a user, to stream a video asset (block 810). For example, application server 210 may receive a request to stream a video asset that has been purchased by the user. A first bookmark, associated with the video asset, may be retrieved from the user's profile (block 820). Application server 210 may determine whether a bookmark is associated with the video asset. For example, a user may have previously started to view the video asset and may have stopped viewing of the video asset at a particular location. Application server 210 may request bookmark information from profile server 245. Profile server 245 may access a record, associated with the video asset, in a library of purchased video assets associated with the user and may determine whether a bookmark is stored in association with the video asset. Profile server 245 may return the bookmark to application server 210.

The first bookmark may be converted to a first range header value (block 830). For example, application server 210 may convert the bookmark into a range header value based on the size of the file associated with the video asset. For example, assume the video asset file corresponds to a size of 2048 MB and the video asset is 90 minutes long. If the bookmark indicates that the user stopped playing the video asset at a location 30 minutes into the video asset, application server 210 may determine a ratio of the video asset length to the length indicated by the bookmark, and generate a range header value based on the ratio. Thus, application server 210 may convert the bookmark information to a range header value of 683/2048. The first range header value may be provided to a video asset player of a browser associated with the user (block 840). For example, application server 210 may provide the first range header value to media player 505 of user device 110.

A second range header value may be received from the video asset player of the browser associated with the user (block 850). For example, the user may pause or stop playing the video asset at a later time and media player 505 may report a range header value associated with the location at which the playback of the video asset was stopped or paused. For example, if the video asset file corresponds to a size of 2048 MB, and the user stopped playing the video asset at a halfway point, application server 210 may receive a range header value of 1024/2048.

The second range header value may be converted to a second bookmark (block 860) and the second bookmark may be stored in the user's profile (block 870). For example, application server 210 may convert the second range header value to a second bookmark and may forward the second bookmark to profile server 245 to store the second bookmark in a video asset record, associated with the video asset, of a library of purchased video assets associated with the user's profile. For example, if the video asset is 90 minutes long, and the second range header value corresponds to 1024/2048, the second range header value may be converted to a bookmark that indicates that playback stopped at a location of 45 minutes from the beginning of the video asset.

While FIG. 8 illustrates an example where conversion between a bookmark and a range header value is performed by application server 210, in another example, the conversion between a bookmark and a range header value may be performed at user device 110 by media player 505.

Figure 9:
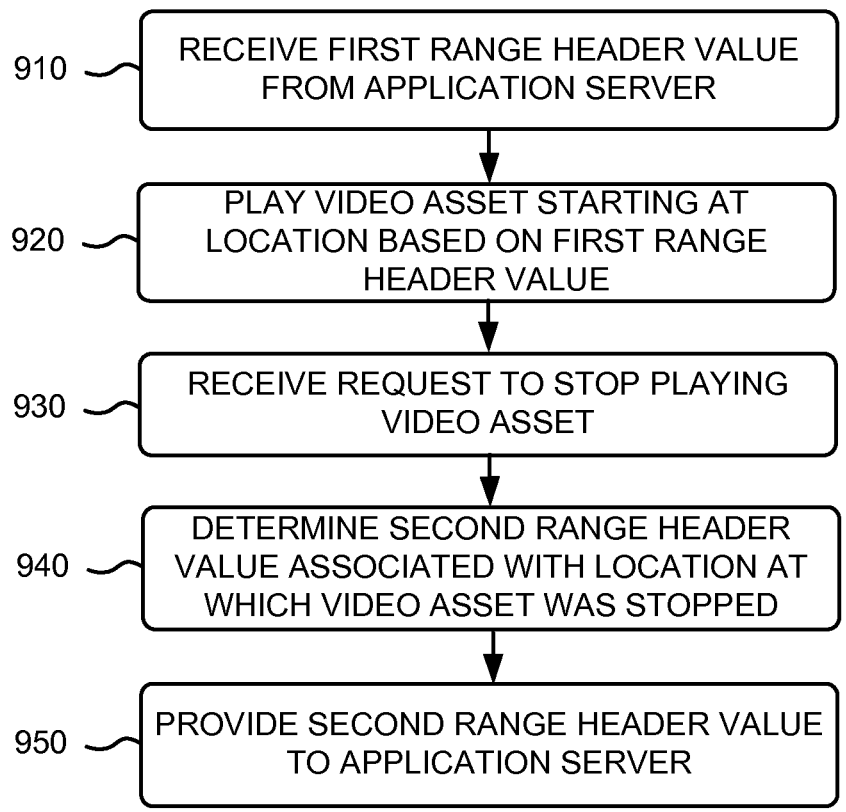
FIG. 9 is a flow chart of an example process for using a bookmark to play a video asset according to an implementation described herein.

FIG. 9 is a flow chart of an example process for using a bookmark to play a video asset according to an implementation. In one implementation, the process of FIG. 9 may be performed by user device 110. In other implementations, some or all of the process of FIG. 9 may be performed by another device or a group of devices separate from user device 110 and/or including user device 110.

The process of FIG. 9 may include receiving a first range header value from an application server (block 910). For example, media player 505 may receive a first range header value from application server 210 in response to requesting to stream a video asset. The first range header value may correspond to a bookmark associated with the video asset. A video asset may be played starting at a location based on a first range header value (block 920). For example, media player 505 may send a request to CDN server 230 to initiate retrieving the video asset at a location specified by the first range header value.

A request may be received to stop playing the video asset (block 930). For example, the user may stop playback of the video asset at a later time by pausing or stopping media player 505. A second range header value, associated with a location at which the video asset was stopped, may be determined (block 940). For example, media player 505 may determine a range header value associated with the location at which the video asset has been stopped. The second range header value may be provided to the application server (block 950). For example, media player 505 may provide the second range header value to VPS 120 (e.g., to application server 210) to be converted to a bookmark that is stored in connection with the video asset in the library of the user's profile.

Figure 10:
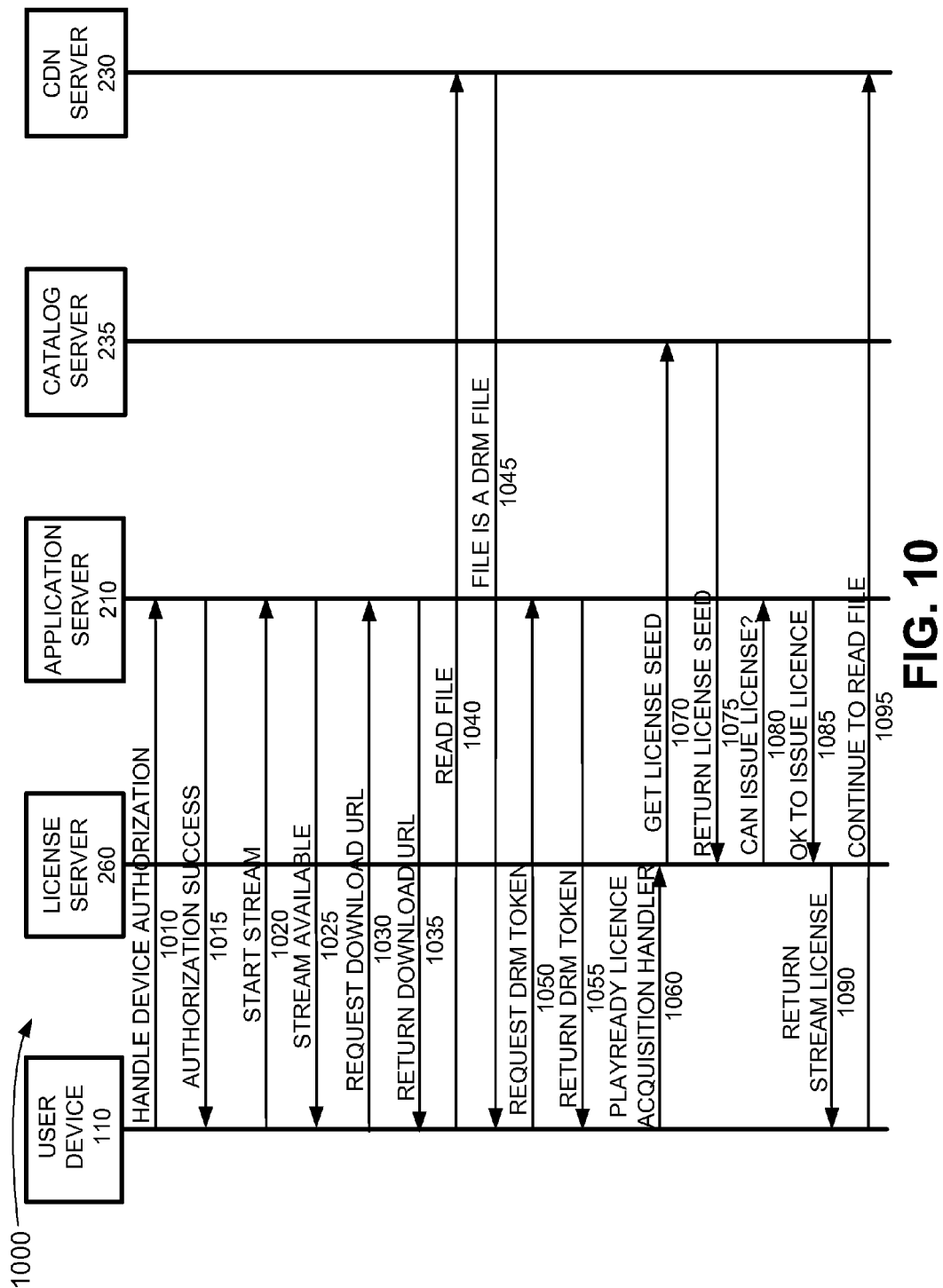
FIG. 10 is a diagram of an example signal flow of a process for managing consumption of a video asset based on multiple digital rights management schemes according to an implementation described herein.

FIG. 10 is a diagram of an example signal flow 1000 of a process for managing consumption of a video asset based on multiple digital rights management schemes according to an implementation described herein. As shown in FIG. 10, example signal flow 1000 may include user device 110 requesting device authorization with application server 210 (signal 1010). For example, a user may activate browser application 500 on user device 110 and may access a web site hosted by application server 210. The user may log in by entering a username and password into a login page associated with application server 210. Additionally, user device 110 may provide a user device identifier to application server 210. The user device identifier may be used by application server 210 to determine whether user device 110 is a registered device associated with the user's VPS account. After authorizing user device 110, application server 210 may confirm that authorization of user device 110 was successful (block 1015).

User device 110 may send a request to application server 210 to start streaming a video asset via browser application 500 (signal 1020). For example, a user may have purchased a video asset using a store front associated with application server 210 at a previous time and may decide to play the video asset in browser application 500 by accessing a library of purchased video assets and selecting to play the video asset. Stream manager 410 of application server 210 may determine whether a stream is available and may indicate to user device 110 that a stream is available (signal 1025). For example, a user may be authorized to have one active stream on a device other than a set top box. Thus, if the user does not have an active stream on any registered devices other than a set top box, application server 210 may indicate that a stream is available.

In response to receiving the indication that a stream is available, user device 110 may request a download URL associated with the video asset (block 1030). Application server 210 may request the URL from catalog server 235 (not shown in FIG. 10), may receive the URL from catalog server 235, and may return the download URL to user device 110 (block 1035). In response, user device 110 may attempt to read the video asset file by accessing the URL at CDN server 230 (block 1040). CDN server 230 may indicate that the video asset file is a DRM file associated with a first DRM scheme (block 1045). For example, CDN server 230 may indicate that the video asset file is encrypted using WMDRM.

In response to receiving the indication that the video asset file is encrypted with WMDRM, user device 110 may request a DRM token from application server 210 (signal 1050). The request may include a username and password associated with the user. Application server 210 may authenticate the user based on the username and password. If the user is successfully authenticated, application server 210 may provide the WMDRM token to user device 110 (signal 1055).

In response to receiving the DRM token, media player 505 may activate, for example, a PlayReady acquisition handler that uses the received DRM token to request a PlayReady license for the video asset (signal 1060). License server 260 may receive the request and may request a license seed from catalog server 235 (signal 1070). Catalog server 235 may receive the request and may access a record, associated with the video asset, which stores metadata associated with the video asset. The metadata may include DRM information associated with the video asset. The DRM information may include a WMDRM key that may be used to decrypt the video asset. The WMDRM key may be provided by catalog server 235 to license server 260 and may be used as a license seed by license server 260 to generate a PlayReady license for the video asset (signal 1075).

After receiving the license seed, license server 260 may request authorization from application server 210 to issue a PlayReady license for the video asset (signal 1080). The request may include the DRM token received from user device 110. Application server 210 may determine whether the DRM token is valid by comparing the DRM token received from license server 260 with the DRM token issued to user device 110. If application server 210 determines that the DRM token is valid, application server 210 may authorize license server 260 to issue the PlayReady license (signal 1085).

In response to receiving the authorization from application server 210, license server 260 may use the license seed received from catalog server 235 to generate the PlayReady license for the video asset and may provide the generated PlayReady license to user device 110 (signal 1090). In response to receiving the PlayReady license, media player 505 of user device 110 may initiate retrieval of the video content file from CDN server 230 and may use the PlayReady license to decrypt the encrypted video content file.

The foregoing description provides illustration and description, but is not intended to be exhaustive or to limit the implementations to the precise form disclosed. Modifications and variations are possible in light of the above teachings or may be acquired from practice of the embodiments.

While series of blocks have been described with respect to FIGS. 6-9, the order of the blocks may be modified in other implementations. Further, non-dependent blocks may be performed in parallel.

It will be apparent that systems and/or methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code--it being understood that software and control hardware can be designed to implement the systems and methods based on the description herein.

Further, certain portions, described above, may be implemented as a component that performs one or more functions. A component, as used herein, may include hardware, such as a processor, an ASIC, or a FPGA, or a combination of hardware and software (e.g., a processor executing software).

It should be emphasized that the terms "comprises"/"comprising" when used in this specification are taken to specify the presence of stated features, integers, steps or components but does not preclude the presence or addition of one or more other features, integers, steps, components or groups thereof.

Even though particular combinations of features are recited in the claims and/or disclosed in the specification, these combinations are not intended to limit the disclosure of the embodiments. In fact, many of these features may be combined in ways not specifically recited in the claims and/or disclosed in the specification. Although each dependent claim listed below may directly depend on only one other claim, the disclosure of the embodiments includes each dependent claim in combination with every other claim in the claim set.

No element, act, or instruction used in the present application should be construed as critical or essential to the embodiments unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A method comprising:

providing, by a video provisioning system, access to a library of purchased video assets to a user device, wherein the video assets were purchased by a user associated with the user device;

receiving, by the video provisioning system, a request to stream a video asset from the library of purchased video assets by a browser application associated with the user device;

authorizing, by the video provisioning system, the streaming of the video asset;

providing, by the video provisioning system, a Uniform Resource Locator for the requested video asset to the browser application, in response to authorizing the streaming of the video asset;

receiving, by the video provisioning system, a request for a first digital rights management token for the requested video asset from the browser application;

providing, by the video management system, the first digital rights management token to the browser application;

receiving, by the video provisioning system, a license authorization request to issue a digital rights management license for the video asset, where the license authorization request is received from a license server, where the digital rights management license is to be used by the user device to decrypt the video asset, and where the license authorization request includes a second digital rights management token;

determining, by the video provisioning system, whether the second digital rights management token matches the first digital rights management token;

authorizing, by the video provisioning system, the license server to issue the digital rights management license for the video asset, when the second digital rights management token matches the first digital rights management token;

retrieving, by the video provisioning system, a bookmark, associated with the video asset, from a video provisioning system profile associated with the user device;

converting, by the video provisioning system, the bookmark to a range header value associated with a range header field of the browser application, wherein the range header value indicates an offset from a beginning of the video asset; and providing, by the video provisioning system, the range header value to the browser application.

2. The method of claim 1, where the video asset is encrypted using a first digital rights management scheme, where the digital rights management license is associated with a second digital rights management scheme, and where the first digital rights management scheme is different from the second digital rights management scheme.

3. The method of claim 2 where the first digital rights management scheme includes a Windows Media Digital Rights Management scheme and where the second digital rights management scheme includes a PlayReady Digital Rights Management scheme.

4. The method of claim 1, further comprising:

receiving a username from the user device;

authenticating the user device using the received username; and wherein providing the first digital rights management token to the browser application is performed in response to authenticating the user device.

5. The method of claim 1, where the first digital rights management token expires after a particular length of time.

6. The method of claim 1, further comprising:

receiving another range header value, associated with the video asset, from the browser application;

converting the other range header value to another bookmark; and storing the other bookmark in a video provisioning system profile associated with the user device.

7. A video provisioning system comprising: one or more server devices configured to:
provide access to a library of purchased video assets to a user device, wherein the video assets were purchased by a user associated with the user device;
receive a request to stream a video asset from the library of purchased video assets by a browser application associated with the user device;
authorize the streaming of the video asset;
provide a Uniform Resource Locator for the requested video asset to the browser application, in response to authorizing the streaming of the video asset;
receive a request for a first digital rights management token, associated with the requested video asset from the browser application;
provide the first digital rights management token to the browser application;
receive a license request from the browser application for a digital rights management license to decrypt the video asset, where the license request includes a second digital rights management token;
determine whether the second digital rights management token matches the first digital rights management token;
authorize the digital rights management license for the video asset to be issued, when the second digital rights management token matches the first digital rights management token;
provide the digital rights management license to the browser application, in response to receiving the authorization;
retrieve a bookmark, associated with the video asset, from a video provisioning system profile associated with the user device;
convert the bookmark to a range header value associated with a range header field of the browser application, wherein the range header value indicates an offset from a beginning of the video asset; and
provide the range header value to the browser application.

8. The video provisioning system of claim 7, further comprising: a catalog server to:
store a key for the video asset, where the key is associated with a first digital rights management scheme used to encrypt the video asset; and
where the one or more server devices are further to:
obtain the key from the catalog server; and
generate the digital rights management license using the obtained key as a license seed, in response to receiving the authorization from an application server of the one or more server devices, where the digital rights management license is associated with a second digital rights management scheme, and where the first digital rights management scheme is different from the second digital rights management scheme.

9. The video provisioning system of claim 8, where the first digital rights management scheme includes a Windows Media Digital Rights Management scheme and where the second digital rights management scheme includes a PlayReady Digital Rights Management scheme.

10. The video provisioning system of claim 7, where the one or more server devices are further to:
receive a username from the user device;
authenticate the user device using the received username; and
where, when the one or more server devices are to provide the first digital rights management token to the browser application, the one or more server devices are to provide the first digital rights management token to the user device in response to authenticating the user device.

11. The video provisioning system of claim 10, where the digital rights management token expires after a particular length of time.

12. The video provisioning system of claim 7, where the one or more server devices are further to:
receive another range header value, associated with the video asset, from the browser application;
convert the other range header value to another bookmark; and
store the other bookmark in a video provisioning system profile associated with the user device.

13. One or more non-transitory media storing instructions executable by one or more processors, the one or more non-transitory media comprising:
one or more instructions to provide access to a library of purchased video assets to a user device, wherein the video assets were purchased by a user associated with the user device;
one or more instructions to receive a request to stream a video asset from the library of purchased video assets by a browser application associated with the user device;
one or more instructions to authorize the streaming of the video asset;
one or more instructions to provide a Uniform Resource Locator for the requested video asset to the browser application, in response to authorizing the streaming of the video asset;
one or more instructions to receive a request for a first digital rights management token, associated with the requested video asset from the browser application;
one or more instructions to provide the first digital rights management token to the browser application;
one or more instructions to receive a license authorization request to issue a digital rights management license for the video asset, where the license authorization request is received from a license server, where the digital rights management license is to be used by the user device to decrypt the video asset, and where the license authorization request includes a second digital rights management token;
one or more instructions to determine whether the second digital rights management token matches the first digital rights management token;
one or more instructions to authorize the license server to issue the digital rights management license for the video asset, when the second digital rights management token matches the first digital rights management token;
one or more instructions to retrieve a bookmark, associated with the video asset, from a video provisioning system profile associated with the user device;
one or more instructions to convert the bookmark to a range header value associated with a range header field of the browser application, wherein the range header value indicates an offset from a beginning of the video asset; and
one or more instructions to provide the range header value to the browser application.

14. The one or more non-transitory media of claim 13, further comprising:
one or more instructions to receive a username from the user device;
one or more instructions to authenticate the user device using the received username; and wherein the one or more instructions to provide the first digital rights management token to the browser application include one or more instructions to provide the first digital rights management token to the user device in response to authenticating the user device.

15. The one or more non-transitory media of claim 13, further comprising:
one or more instructions to receive another range header value, associated with the video asset, from the browser application;
one or more instructions to convert the other range header value to another bookmark; and
one or more instructions to store the other bookmark in a video provisioning system profile associated with the user device.

* * * * *